United States Patent [19]

Csatary et al.

[11] 3,996,932
[45] Dec. 14, 1976

[54] INTRA-UTERINE CONTRACEPTIVE DEVICE

[76] Inventors: Laszlo Kalman Csatary, 1913 Windsor Road, Alexandria, Va. 22307; Frank Istvan Pongracz, 10833 Margate Road, Silver Spring, Md. 20901

[22] Filed: May 15, 1975

[21] Appl. No.: 577,864

Related U.S. Application Data

[62] Division of Ser. No. 451,742, March 18, 1974, Pat. No. 3,933,153.

[52] U.S. Cl. .............................. 128/129; 128/130
[51] Int. Cl.² .......................................... A61F 5/46
[58] Field of Search .......................... 128/127–131, 128/260

[56] References Cited
UNITED STATES PATENTS

| 3,256,878 | 6/1966 | Schwartz | 128/130 |
| 3,405,711 | 10/1968 | Bakunin | 128/130 |
| 3,756,228 | 9/1973 | Lerner | 128/130 |
| 3,785,376 | 1/1974 | Kitrilakis | 128/130 |
| 3,786,808 | 1/1974 | Lerner | 128/130 |

*Primary Examiner*—Lawrence W. Trapp

[57] ABSTRACT

An intra-uterine contraceptive device of the inflatable type provided with a plurality of protrusions for providing an unimpeded passage of the menstrual flow, such protrusions in one embodiment are wave-like configurations and in other embodiments they are arm-like extensions for providing also a plurality of contact regions with the inner wall of the uterus.

7 Claims, 5 Drawing Figures

INTRA-UTERINE CONTRACEPTIVE DEVICE

This is a division of application Ser. No. 451,742, filed Mar. 18, 1974, now U.S. Pat. No. 3,933,153.

FIELD OF THE INVENTION

The present invention relates generally to intra-uterine contraceptive devices, known as I.U.D., and more particularly it relates to inflatable I.U.D. having improved shape and insertion possibilities.

BACKGROUND OF THE INVENTION

I.U.D.'s used for the purpose of contraception are old in art, having been popularized by the development of Dr. Ernst Grafenberg's silver ring. Since that time, almost 40 years ago, there have been many improvements in both the configuration and the material of the device as well as the efficiency and the public acceptance of the device. The configuration of the I.U.D.'s most frequently used today may be categorized generally as coils, loops, rings and bows, the best known examples being those devices developed by Margulies, Lippes, Ota and Birnberg, respectively.

It has long been recognized that even though I.U.D's are safe, reliable and efficient, there are still several very important structural aspects that can be improved. For example, the I.U.D. must be capable of insertion using a thin-walled cannula and a push rod without the need for dilation of the cervix, such as described in U.S. Pat. No. 3,628,530 issued on Dec. 21, 1971 to Jerome Schwartz.

It has also been recognized that although the I.U.D. must be readily removable, if possible without surgical interference, yet it must be capable of resisting expulsion caused by the involuntary uterine contractions exhibited by the fundus muscle. These are, of course, diametrically opposite conditions, but which must nevertheless be met for the I.U.D. to be effective.

It has also been recognized that the I.U.D. for proper reliability must have a maximum contact with the walls of the uterus, which belief lead to the inflatable types closely conforming to the shape of the uterus, such as described in U.S. Pat. No. 3,452,749 issued July 1, 1969 to Edwin H. Riedell.

In U.S. Pat. No. 3,464,409 issued on Sept. 2, 1969 to James Murphy an I.U.D. is described which is inflatable through a tube after it has been inserted into the uterus and expands into a balloon-like configuration having pouch-like expansions around the periphery of the main balloon.

In U.S. Pat. No. 3,401,689 issued on Sept. 17, 1968 to Eugene C. Greenwood, a smooth-walled toroidal-shaped I.U.D. is described which is introduced into the uterus in a deflated condition and becomes inflated through a syringe.

In U.S. Pat. No. 3,782,376 issued on Jan. 1, 1974 to Irwin S. Lerner, an I.U.D. is described which is provided with spurs directed toward the cervix to prevent expulsion of the I.U.D.

It has not been, however, recognized that contact with the inner walls of the uterus is desirable rather at a plurality of smaller regions than at large surfaces in order to minimize irritations of the inner wall of the uterus and to avoid blockage of the menstrual flow. At the same time an I.U.D. answering the above requirements must have retained the last mentioned beneficial properties even under the expulsionary effects of the fundus and in addition assume a shape which laterally increases its size with respect to the cervix under the last-mentioned conditions and reliably prevents thereby its expulsion.

SUMMARY OF THE INVENTION

It is, therefore, an object of the present invention to provide an improved and novel contraceptive device, hereinafter called I.U.D. device, which can be inserted into the uterus relatively easily without requiring medical attention and which does not interfere with the normal physiological processes, such as the menstrual flow, of the female body and which is capable of resisting explusionary forces of the uterus.

It is another object of the present invention to provide an improved and novel I.U.D. device of the above described type which due to its shaping will contact the inner walls of the uterus at a plurality of regions in a resilient manner instead of presenting a large homogeneous surface pressing against the inside of the uterus as is the case in some of the heretofore known inflatable I.U.D. devices.

It is still another object of the present invention to provide a novel and improved I.U.D. device of the above-described inflatable type which comes on the market in an inflated form and is ready for insertion with the help of an appropriate inserting device without need for the dilation of the cervix.

It is a further object of the present invention to provide an improved and novel inflatable I.U.D. device which has a fluid filling material having a color code which readily indicates if the I.U.D. device has burst in situ, by virtue of the color coded fluid leaving the uterus.

It is still a further object of the present invention to provide an improved and novel I.U.D. which reaches the market in a deflated form packed into an inserting assembly together with an inflating syringe and which is inflated upon insertion into the uterus and filled with a gas or a color coded liquid for the purpose as hereinbefore described.

It is still a further object of the present invention to provide an improved and novel I.U.D. device of the above described type which is provided with a control means extending through the cervix and which serves for the removal of the I.U.D. device if so desired, and which improved I.U.D. device according to the present invention contains an X-ray sensitive material lending to it a character of easy recognition of the I.U.D. device during an X-ray process.

BRIEF DESCRIPTION OF THE DRAWINGS

The present invention will become more readily apparent from the following description of the preferred embodiments thereof shown in the accompanying drawings, in which.

DESCRIPTION OF THE PREFERRED EMBODIMENTS

Figure 1:
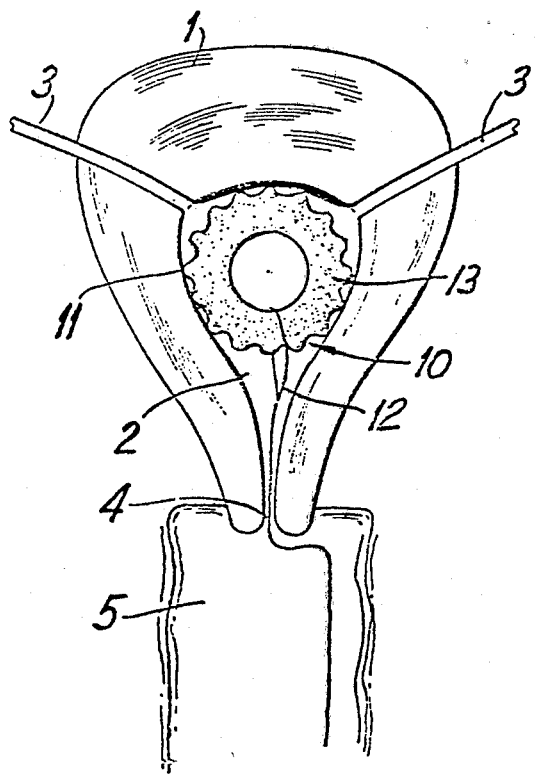
FIg. 1 is a schematic illustration of one of the embodiments of the I.U.D. device according to the present invention in situ within the uterus.
Figure 2:
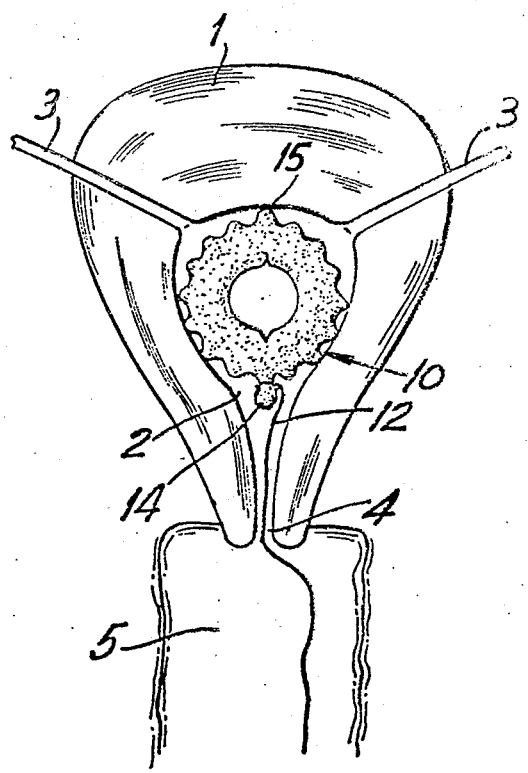
FIg. 2 is a similar illustration as FIG. 1 illustrating another embodiment of the I.U.D. device according to the present invention.
Figure 3:
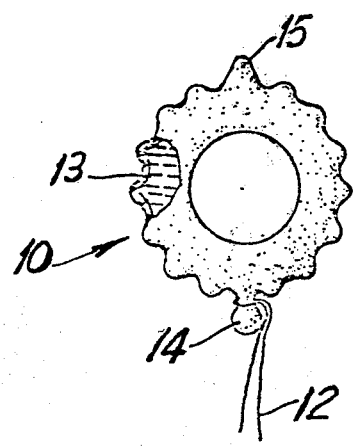
FIG. 3 is an illustration of the I.U.D. device of FIG. 2 in section.

With reference to FIGS. 1-3 illustrating the so called donut-shaped I.U.D. devices according to the present invention, it is noted that FIG. 1 is a schematic representation of the uterus 1 and the adjacent parts of the female body, such as the internal part 2 of the uterus 1 which communicates by means of tubes 3 with the ovaries, not shown, and through the cerivx 4 with the vagina 5. The first embodiment 10 of the I.U.D. device according to the present invention is illustrated in situ and which is made into donut shape and generally having the overall diameter of about 25 mm. The hollow internal void in the donut is made large enough, about 15 mm. so that the menstrual flow can pass without hindrance toward the cervix 4 and into the vagina 5. The donut-shaped I.U.D. 10 is made from flexible biologically inert synthetic material, preferably from teflonized rubber containing a certain amount of barium sulfate in order to lend X-ray sensitivity to the I.U.D. device 10 in order that it could be detected by X-ray. Other plastic materials which also may be employed are polyethylene, polypropylene, ethylene, propylene, copolymers, EPT, silicone rubber, etc. The I.U.D. device is made in one single molding step and is filled with an inert gas, but it can also be filled with air, or with a liquid material which preferably according to the present invention, is an antiseptic dye stuff having a color distinctly other than the menstrual flow in order to provide an indication to the user of the I.U.D. device in the event it has burst and the liquid has been passed. The shape of the donut I.U.D. device 10 is such that it is provided with a plurality of wave-like corrugations 11 about its entire circumference in order to provide a plurality of contact regions with the walls of the uterus 2 aiding thereby the menstrual flow and in order to avoid the situation that the I.U.D. device 10 would stick to the wall of the uterus 2 over a large surface where it could prevent passage of the menstrual flow or cause other undesirable effects due to the large contact surface, such as lend itself to internal strangulations. As can be seen in FIG. 1, a removing or control string 12 is attached to the I.U.D. device 10 in order to facilitate the removal of the I.U.D. device 10 if desired. The removing string 12 extends through the cervix 4 into the vagina 5 and it is easily detectable. The nature of the material from which the I.U.D. device is made and due to the resilient behaviour of the inflating inert gases or of the liquid contained in the I.U.D. device 10, the removal of the donut-shaped I.U.D. device 10 is relatively painless since a strong pull on the removing string 12 will change the shape of the I.U.D. device 10 into an elongated oval shape pointing downwardly and will pass through the cervix 4 without requiring a dilation of the cervix 4. On the other hand, the fact that the I.U.D. device 10 is donut shaped, any expelling natural process of the uterus 1 exerted onto the I.U.D. device 10 by the fundus of the uterus 1 will change the shape of the I.U.D. device 10 into an elongated oval which on the other hand, extends transversely within the uterus 10, therefore cannot pass through the cervix 4 since the longer lateral side of the I.U.D. device 10 will be facing the cervix 4 itself under such conditions.

With reference to FIG. 2 it is noted that the general shape of the I.U.D. device 10 illustrated therein is somewhat different from the donut shape of FIG. 1, however, it is still generally donut-like having the large internal void and the wave-like ondulations 11 of its shape about its circumference. It has also a larger corrugation or protrusion 15 at the top and having a leg-like protrusion 14 at the bottom to which the removing string 12 is attached. In order to safely attach the removing string 12 to the leglike protrusion 14, it is preferred to make it solid from the general material of the I.U.D. device 10 so that a firmer pulling force could be applied to the I.U.D. device 10 through the string 12 in the event removal is desired. The material and characters of the I.U.D. device of FIG. 2 are similar to that described in connection with FIG. 1 and it is illustrated in closer detail in cross-section in FIG. 3.

Figure 4:
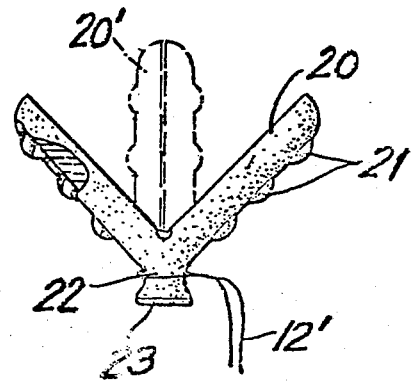
FIGS. 4 and 5 illustrate additional embodiments of the I.U.D. device according to the present invention.
Figure 5:
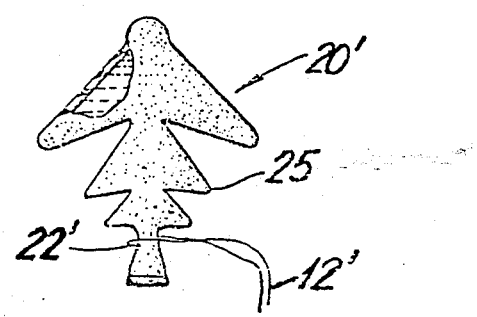

With reference to FIGS. 4 and 5 illustrating other embodiments of the I.U.D. device of the present invention it is seen that the I.U.D. device 20 of FIG. 5 when inserted into the uterus 2, and then becomes inflated as hereinafter described, expands into a generally V-shaped form with the tips and outer parts of the V-shape touching the internal walls of the uterus inner space 2. The I.U.D. device 20 of FIG. 4 is provided also with bead-like corrugations for the same purpose as the I.U.D. device described in connection with FIGS. 1, 2 and 3. Before insertion into the uterus 2 in the packed form, the I.U.D. device 20 assumes the shape 20' within an associated inserting device. The I.U.D. device 20 has also a leg-like protusion 23 connecting the V-shaped arms 21 through a neck portion 22 to which the removing string 12' is attached. The bottom of the leg-like protrusion 23 contains a self-sealing valve mechanism which is well known in the art and which receives the needle of a syringe for inflation or filling purpose and when the needle is removed it will tightly reseal the I.U.D. device 20 so that it retains the inert gas or liquid inserted thereinto without loss.

With reference to FIG. 5, illustrating another embodiment of the I.U.D. device according to the present invention, it is seen that the I.U.D. device 20'' illustrated therein has a generally christmas tree shape having a plurality of arm-like protrusions 24 and 25 which extend laterally when the I.U.D. device 20'' becomes inflated or filled with a liquid and which come in contact with the walls of the uterus 2. The self-sealing valve means 23' is similar to the one described in connection with FIG. 4. Other similar parts are designated by the reference numerals 12' and 22'.

I wish it to be understood that I do not desire to be limited to the exact details of construction shown and described, for obvious modifications will occur to a person skilled in the art.

Having thus described the invention, what I claim as new and desire to be secured by Letters Patent, is as follows:

1. An intra-uterine contraceptive device comprising an annular hollow body made from a biologically inert flexible material, a fluid filling said body, a plurality of wave-like smooth rounded-off protusions formed on the outer surface of said body substantially about the entire circumference thereof, for providing a plurality of contact regions with the inner wall of the uterus when said contraceptive device is inserted into the uterus but allowing free spaces left between adjacent wave crests and between the inner wall of the uterus.

2. The contraceptive device as claimed in claim 1, wherein said fluid is air.

3. The contraceptive device as claimed in claim 1, wherein said fluid is an inert gas.

4. The contraceptive device as claimed in claim 1, wherein said fluid is an antiseptic dye stuff having a color other than the color of the menstrual flow.

5. The contraceptive device as claimed in claim 1, wherein said annular body has a central opening therethrough for allowing an unobstructed passage of the menstrual flow through said contraceptive device.

6. The contraceptive device as claimed in claim 1, including a string means attached to said annular body for allowing removal of said contraceptive device through the cervix when desired.

7. The contraceptive device as claimed in claim 1, wherein said annular body includes at least one protrusion larger than said wave-like protrusions a removal string attached to said protrusion for allowing removal of said contraceptive device through the cervix when desired.

* * * * *